United States Patent
Bayramov

(10) Patent No.: US 9,055,990 B1
(45) Date of Patent: Jun. 16, 2015

(54) BAYRAMOV'S OPEN FRAMEWORK DENTURE AND METHOD FOR MANUFACTURING THE SAME

(71) Applicant: Meret Bayramov, Ashgabat (TM)

(72) Inventor: Meret Bayramov, Ashgabat (TM)

( * ) Notice: Subject to any disclaimer, the term of this patent is extended or adjusted under 35 U.S.C. 154(b) by 0 days.

(21) Appl. No.: 14/217,632

(22) Filed: Mar. 18, 2014

(51) Int. Cl.
  *A61C 13/08* (2006.01)
  *A61C 13/02* (2006.01)
  *A61K 6/04* (2006.01)
  *A61C 13/097* (2006.01)
  *A61C 13/083* (2006.01)

(52) U.S. Cl.
  CPC . *A61C 13/02* (2013.01); *A61K 6/04* (2013.01); *A61C 13/097* (2013.01); *A61C 13/0835* (2013.01)

(58) Field of Classification Search
  CPC .... A61C 13/08; A61C 13/081; A61C 13/085; A61C 13/097
  USPC .............. 433/218, 219, 223, 202.1, 206, 208
  See application file for complete search history.

(56) References Cited

U.S. PATENT DOCUMENTS

| | | | | |
|---|---|---|---|---|
| 4,846,718 A | * | 7/1989 | Rieger | 433/180 |
| 5,186,626 A | * | 2/1993 | Tanaka | 433/180 |
| 5,308,243 A | * | 5/1994 | Emmons | 433/203.1 |
| 5,332,622 A | * | 7/1994 | Shoher et al. | 428/323 |
| 5,730,600 A | * | 3/1998 | Shoher et al. | 433/223 |
| 5,951,293 A | * | 9/1999 | Billet et al. | 433/218 |
| 6,506,054 B2 | * | 1/2003 | Shoher et al. | 433/223 |

FOREIGN PATENT DOCUMENTS

DE   3243020 A1 *  5/1984

* cited by examiner

*Primary Examiner* — Ralph Lewis
(74) *Attorney, Agent, or Firm* — Nadya Reingand

(57) ABSTRACT

A dental prosthetic device and a method for its fabrication are disclosed. The method is applicable for metalloceramics or metalloplastics permanent dentures based on a light metal openwork frame strengthened by multiple layers of ceramic or plastic custom coating.

15 Claims, 7 Drawing Sheets

(a)

(b)

(a)          (b)

BAYRAMOV'S OPEN FRAMEWORK DENTURE AND METHOD FOR MANUFACTURING THE SAME

REFERENCE TO RELATED APPLICATIONS

This patent application claims priority to U.S. Provisional application Ser. No. 61/802,835 filed Mar. 18, 2013.

FIELD OF INVENTION

The invention is related to dentistry, in particular, to the orthopedic dentistry in the area of prosthetics and micro-prosthetics and can be used for manufacturing permanent prosthetic dentures made of combinations of metal and plastic and/or metal and ceramics.

BACKGROUND OF THE INVENTION

A denture is defined herein as a prosthetic device that us constructed to replace missing teeth. The denture is supported by the surrounding tissues of the oral cavity and can be removable or rely on bonding or clasping onto teeth or dental implants.

Restorative dentistry is a blend of science and art. The success of restorative dentistry work is determined on the basis of functional and esthetic results. To achieve this, four the basic determinants are required, viz., structural strength, longevity, position, contour, texture, color and efficient design/manufacturing.

A dental bridge armature has been previously reported, for example in US20130252203, see FIG. 1, where the reinforcing fibrous elements are designed to be screw-fastened on the dental implants with reinforcing element. The method discloses the installation of bridge armature directly on implants for a temporary reinforcement and stabilizing the group of implants, which, apparently, reduces the risk of complications and implant's rejection. This method is not applicable for a long-term (permanent) dental prosthetics.

The use of ceramic fiber as an reinforcing element in dental restoration is suggested by in WO94/08783. Such method is only effective where a single tooth is missing, namely for micro-prosthetics (inlay, onlay, semi-crown).

The method disclosed in WO2088986 suggests application of textured (grid-based) cap without having supporting elements of the dental prosthetic construction. The method is also applicable for a single tooth restoration only.

U.S. Pat. No. 6,200,136 suggests using a fiber-reinforced polymer composition for a missing tooth restoration. The method is not efficient for a bridge-type denture with multiple (5-8) teeth missing.

Alternatively, the use of the soft composite veneer is suggested in U.S. Pat. No. 6,362,250. Using of soft fiber veneer, however, is not preferable for reinforced prosthetic frame.

The method disclosed in WO 2004/100816 suggests the use of intermediate flexible fiber (T-shaped, etc.) structures to reinforce the composite material or plastics. Such T-, O-, and I-shaped beam structures are convenient for replacing of 2-3 teeth only and not efficient for 5-8 teeth denture structures.

There is a known method of dental ceramic coating using an 'Ivoclar' composition. Ivoclar Vivadent is a leader in innovative materials and processes for quality, esthetic dentistry. The method is based on a single coating by the prime (opaque) composition and by a single coating dentine composition alone with an intensive coloring of the dentine. The disadvantage of this method is the reduced aesthetic effect of the denture.

Another well-known ceramic coating method uses a similar standard technology of partial coverage by ceramics layers, typically at the tooth neck area and in the chewing surfaces of molars and incisors. A disadvantage of such cap-sintering (multiple kiln firing) is in developing chips within the ceramic material in 10-15% of cases, which often doesn't meet standards of a modern cosmetic dentistry.

The method of plastic reproductions retaining crowns applied to the metalloceramic frame has been previously reported. Such method is based on the plastic reproductions of retaining crowns that are set on a model, where the intermediate part of the prosthetic bridge is wax-modeled. Then, this part is glued together with a supporting cup (dome) element. Such pre-made plastic-wax structure is removed from the model and replaced by a metal. The disadvantages of this method are the following: i) is not considering a natural volumetric shrinkage of the metal, and ii) as well as lack of a proper alignment of the structure on the natural teeth and also, indirectly, on the model.

There is still an unmet need for new, improved dental prosthetics methods which would benefit from the improved mechanical and cosmetic characteristics, smaller weight, better static and dynamic strength, minimal shrinkage and post-correction and can be used either for a single tooth restoration or multiple teeth permanent bridge dentures work.

SUMMARY OF THE INVENTION

Disclosed a dental prosthetic device (denture) which is based on a metal (or alternative to the metal crystalline glass-ceramic composition) openwork (so called Bayramov's) frame of a fachwerk pattern and a subsequent multi-layered ceramic coating. The device also includes an anchor-keyed mechanism that is engaged between the frame and the coating.

The multi-layered ceramic coating, in turn, includes a basic prime opaque layer, a prime horizontal opaque layer that is matched to a color palette, a first vertical 3:1-ratio-mixed opaque-dentine composition layer, a second horizontal 2:1-ratio-mixed prime opaque-dentine composition layer, a 3:1-ratio-mixed dentine layer made of a main and an auxiliary dentine, respectively and a transparent layer.

The invention also describes a method for manufacturing of such a denture, including a tooth preparation, the tooth preparation.

The preparation includes a manual outlining of a conical shape of the a stump, a 135-degree ledge at the teeth neck area, a 135-degree ledge at the equator area of the teeth, a customization of a natural tooth into a stump for the Bayramov's frame, making an accurate diagnostic impression of the tooth area, a tooth dissection with the 135-degree ledge at the teeth neck area and the 135-degree ledge at the equator area of the teeth, a fabrication of and individually customized plastic mesh-tray with a canopy, a fabrication of a an accurate cast impression made of a silicone putty, a fabrication of a shrink-compensated cast stump from the cast impression, a fabrication of a circular engraving 0.1-0.15 mm below the limits of the teeth's neck area.

The preparation also includes a pencil drawing on the shrink-compensated cast stump being drawn on 3 sides of the shrink-compensated cast stump, including the pencil drawing of a fachwerk pattern and a garland, a fabrication of a wax reproductions of the Bayramov's frame, a fabrication of a main model and an additional control model of the Bayramov's frame and an application of multi-layered ceramic coating to Bayramov's frame.

DETAILED DESCRIPTION OF THE PREFERRED EMBODIMENT

Figure 1:
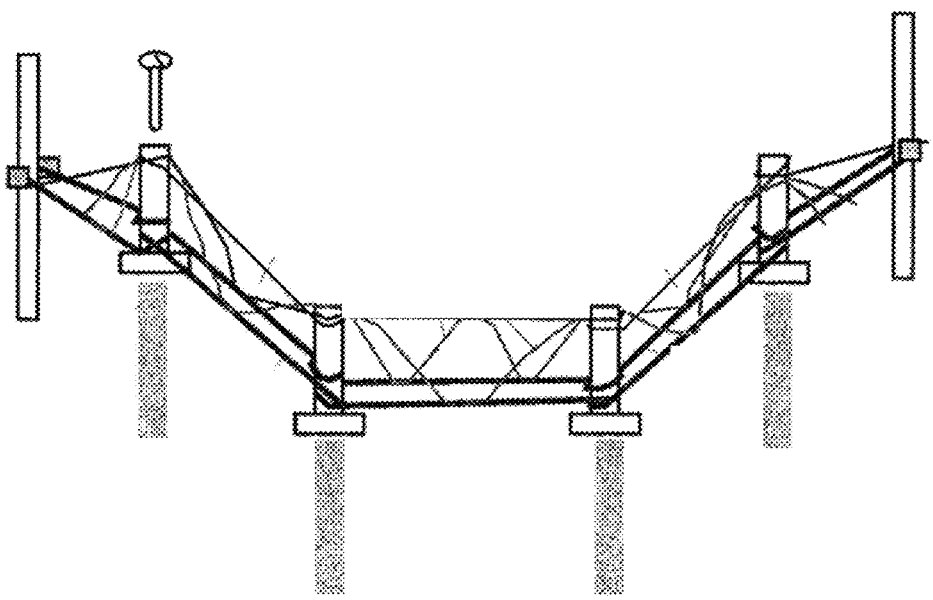
FIG. 1 shows the art prior to the disclosure.

The disclosed invention is based on the openwork metal frame denture, hereinafter called the Bayramov's frame. Such novel method for obtaining a wax reproduction for permanent metal-ceramic (or metal-plastic) restoration dentures based on a metal openwork frame, includes: i) 30% reduction of the resulting weight of the denture, ii) a wax replication of the metallic openwork supporting frame, iii) high strength ceramic (or plastic) coating that is placed on the denture frame, iv) simplicity and convenience of implementation. The essence of the method is twofold:

1. Produce a wax reproduction of openwork metal frame (so-called the Bayramov's frame), followed by waxes substitution by a metal, to produce a set of cast-linked pylons, latches and skeleton-like frames that are all connected by a technical elements, forming a 3-dimentional, lightweight, cast-open structure.

2. A further method to obtain a wax reproduction for permanent (irremovable) metal-ceramic restorations dentures that are placed on a disclosed metal openwork frame. This includes a novel ceramic coating that is placed on the denture frame and generally relates to dentistry, in particular, to orthopedic dentistry in the area of prosthetics and micro-prosthetics and can be used for mass manufacture of fixed dentures made of metal-ceramic or metal-plastic.

Unlike to conventional dental prosthetics methods, the disclosed method eliminates the post-fabrication volumetric shrinkage of the metal. This is achieved by: i) conditioning of the dynamic impact strength, and ii) negligible change in thermal expansion coefficient that affects the strength of the bond between the frame and the ceramic body. The advantage of the disclosed method is the minimal post-correction of the cast metal frame, absence of shrinkage and very strong mechanical ceramics-metal ligament.

The Bayramov frame is defined herein as a set of cast-linked pylons, latches and skeleton-like frames that are all connected by technical elements, forming a 3-dimentional, lightweight, cast-open structure. It includes multiple openings (windows), ledges, and joints that are practically repeating the form of the tooth.

The disclosed Bayramov frame is 30-40% lighter than a similar lump structure and has several advantages, namely:

i) the partial reduction of the structural weight of the denture and, as a result, partial relief the related mechanical stresses without compromising the denture strength characteristics;

ii) it allows for better preserving the dental tissue during the tooth dissection and preparation. This feature is achieved due to engaging the anchor-keyed mechanism. The anchor-keyed mechanism is defined herein as a secure fastening of the metal openwork frame with a forthcoming ceramic layers (a primer/dentin bonding), resulting in forming of a monolithic structure. Such monolithic structure is efficient in preventing the cracks in the coating layer during ceramics sintering, which, in turn, increases the lifetime of the denture.

Figure 7:
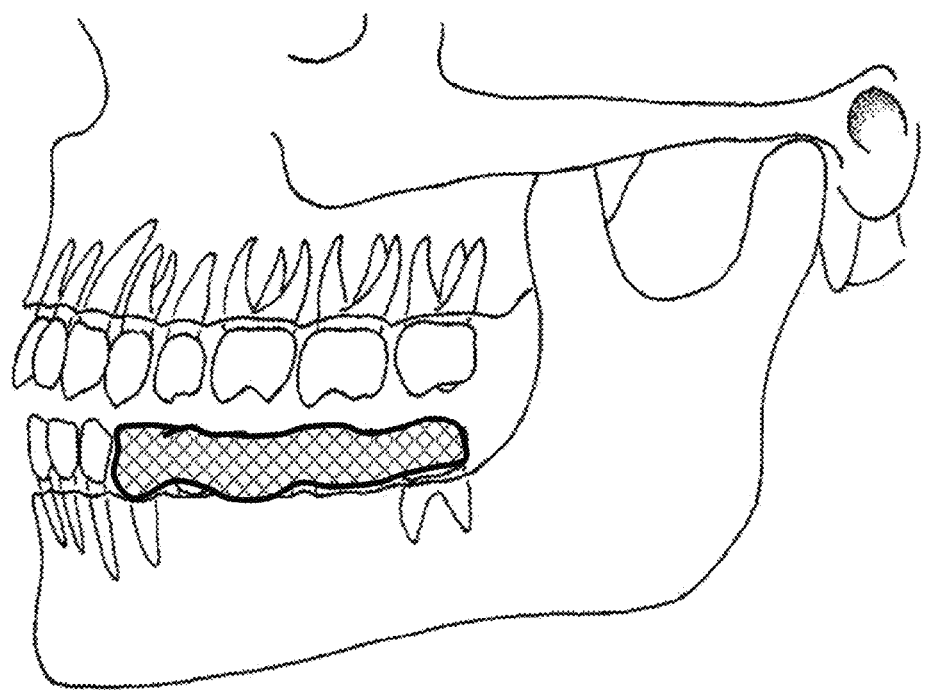
FIG. 7 shows the Bayramov's openwork frame applied to a bridge-type denture when multiple teeth are missing.

The main advantage of the disclosed method is providing a wax reproduction design for metal structure of the denture open-frame (i.e. Bayramov's frame) to increase the mechanical strength of the further ceramic coating and reduce the structural weight by 30%. The method is applicable to single-teeth permanent dentures as well as to a multiple (bridge) permanent prosthetic dentures, see FIG. 7.

Figure 2:
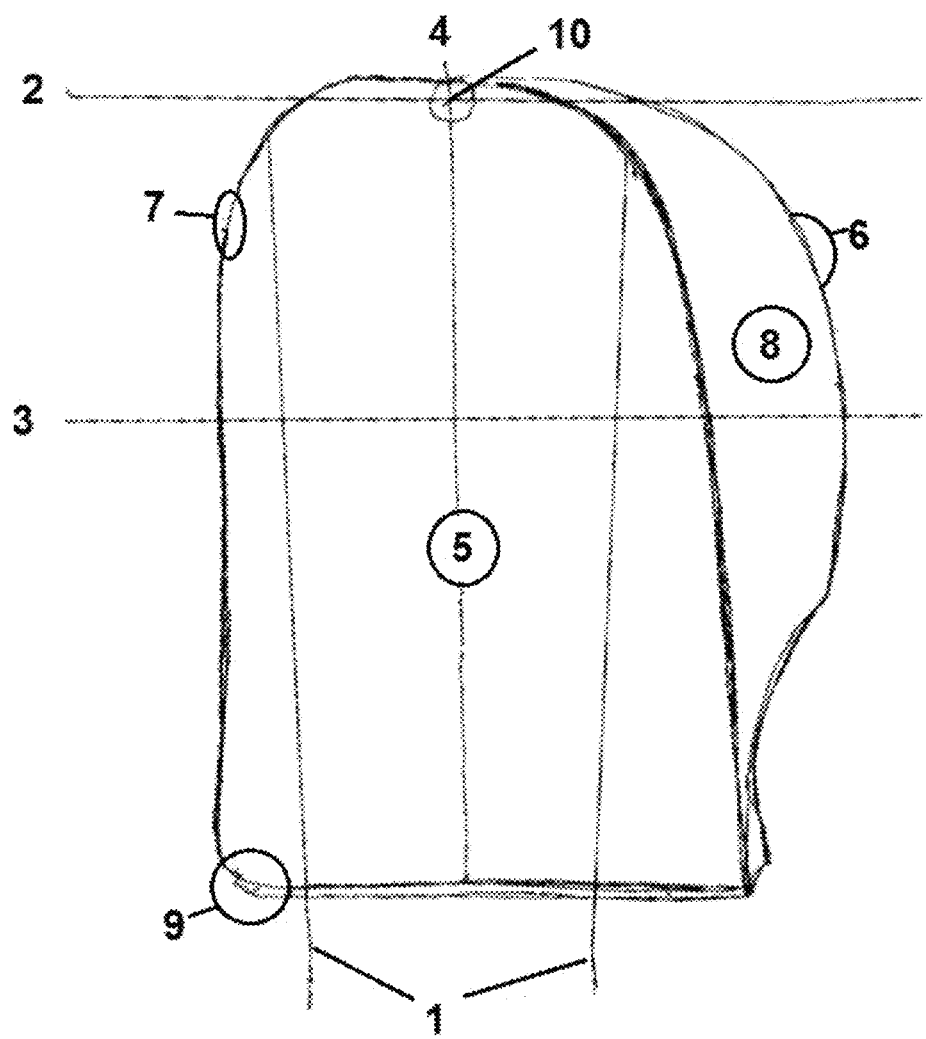
FIG. 2 shows the tooth before preparation.

The tooth before preparation is shown in FIG. 2 includes the manual outlining procedure, where 1—is the line to form the shape of the stump having a 5 degree conical shape; 2—is the line to form a 135-degree ledge at the teeth neck area; 3 the line at for the forming a 135-degree ledge at the equator area of the teeth; line 4 the tooth median line; 5 and 6 is the vestibular and oral surfaces of the tooth, respectively; 7 is the medial surface; 8 is a proximal surface; 9 is the cutting edge of the tooth and 10 is the tooth's neck area. It is assumed that the anatomy of the tooth is well known to the skilled in the art.

Figure 3:
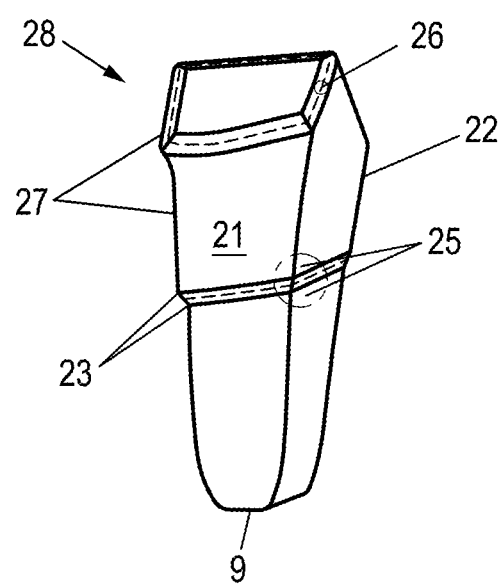
FIG. 3 shows the tooth after preparation.

The tooth after preparation is shown in FIG. 3 as a stump 28, where 21 is a vestibular surface, 22 is the oral surface, 23—is the mentioned 135-degree ledge at the tooth's equator level, 9 is the cutting edge, 27 is the medial surface. 25 is a distal surface, 26 is the mentioned 135-degree ledge at the tooth's neck level. Such ledge at the at the tooth's equator level efficiently reduces the loading at the at the tooth's neck level ledge, which, in turn, reduces the amount of the removed tooth tissue during the stump preparation.

Figure 4:
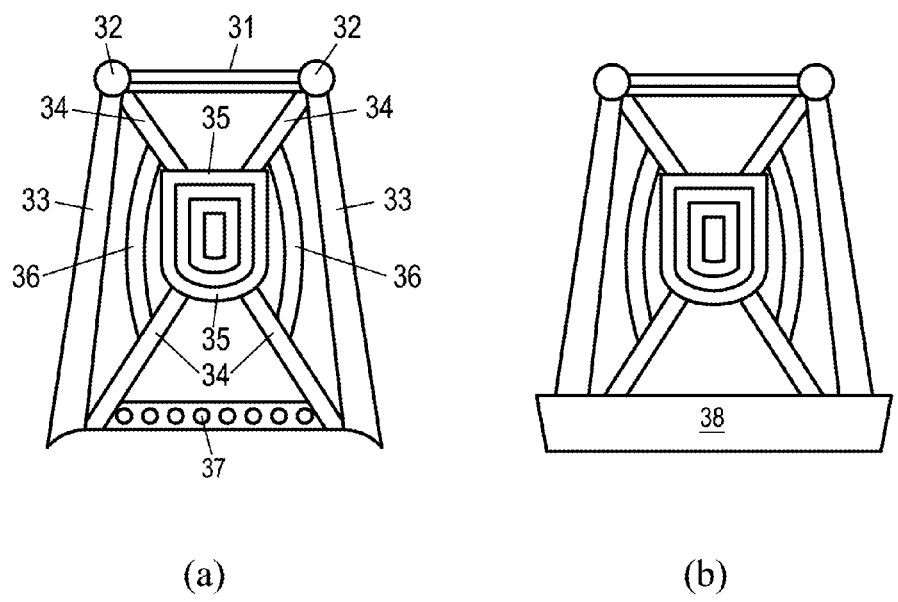
FIG. 4 The proposed (Bayramov's) openwork frame, front and back views.

The proposed openwork frame is shown in FIG. 4 with the vestibular (front) in FIG. 4a, and oral (back) in FIG. 4b.

With the reference to the FIG. 4a. 31 is the upper latch with undercut in a dovetail shape, 32—pearls for better adhesion of ceramics to the framework. 33—Pylons, 34 Diagonal beams, 35—Fachwerk structure, 36—diagonal struts, 37—lower latch to reinforce the ceramic-metal locking at the tooth's neck level ledge to avoid ceramics breaking and enabling mechanical post-treatment of the fabricated crown.

With the reference to the FIG. 4b; 38 is a garland which is an element of the openwork frame. Is necessary to remove the heat during the manufacturing in order to prevent ceramics cracks and chips. For this purpose, the garland has a "dovetail"-shaped ledge to provide good heat dissipation through a butt-joint (without ceramics overlaps that can crack due to a thermal shock).

TABLE 1

| Layers | Main Color | | Auxiliary color | |
| --- | --- | --- | --- | --- |
|  | Prime % | Dentine % | Prime % | Dentine % |
| 1 | 50 | — | 50 | |
| 2 | 75 | — | 75 | |
| 3 | 37.5 | 12.5 | 37.5 | 12.5 |
| 4 | 16.5 | 44 | 16.5 | 22 |
| 5 | — | 75 | | 25 |
| | | Transparent layer | | |

Figure 5:
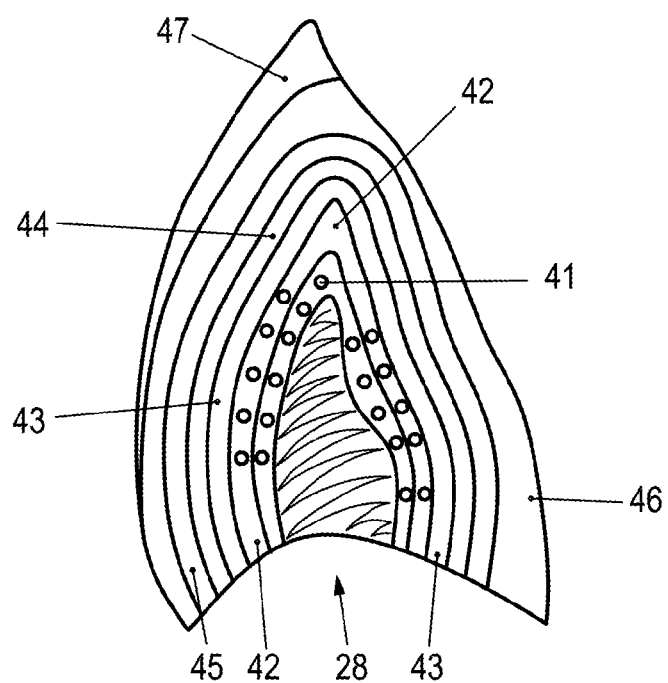
FIG. 5 shows the ceramic layers for openwork frame.

FIG. 5 shows the ceramic layers for openwork frame, where 41 is the openwork (Bayramov's) frame, 42 is the basic prime (opaque) layer that include the filled windows of the frame and vertical application of the first thin opaque layer, 43 is the prime layer with horizontal application matched to color palette from the Table 1 (shows the color palette chromatic distribution of Kerascop by Ivoclar), 44 is the vertically applied layer of a mixed prime-dentine composition in the 3:1 ratio, 45 is the horizontally applied layer made of a mixed prime-dentine composition in the 2:1 ratio, 46 it the vertically applied layer made of a mixed main and auxiliary dentine composition in the 3:1 ratio, 47 is the transparent layer, 28 is the stump of the tooth.

Figure 6:
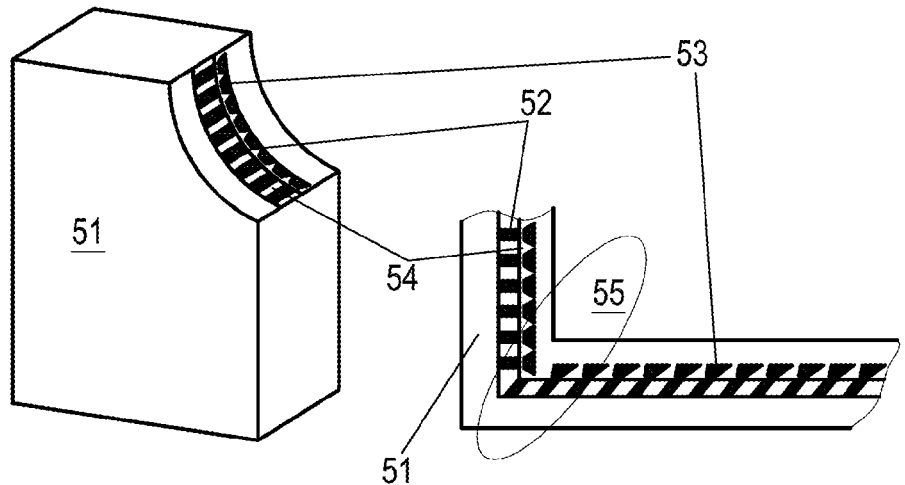
FIG. 6 shows the metallic openwork frame with the ceramic coating.

FIG. 6 shows the metallic openwork frame with the ceramic coating, where 51 is the ceramic layers, 52 the Bayramov's openwork frame, 53 it the prime and dentine compositions, 54 are the windows in the frame that are filled by the prime composition, and 55 is the prime-dentine 'lock' (anchors keyed mechanism) that is locked with the openwork frame. The anchor mechanism is a physical anchor that is made to perform a turn of about 90 degrees from the side part of the frame to the upper tooth part.

The disclosed method can further be described in details. The Initial Steps of the Method.

i) during the first visit of the patient, a specific preparation is taking place to customize the natural tooth (or teeth) to the metal openwork frame resulting in a precise diagnostic impression of the area.

The preparation (dissecting, turning) of the tooth results in a customized stump to be used as a support for the openwork Bayramov's frame, see 28. FIG. 3. Such preparation (dissection; turning) requires a forming of 135-degree ledge at the tooth's equator area in order to avoid potential ceramic flaking at the teeth' neck area, as well as to remove the load from the tooth structure, as shown in FIG. 2. In addition, a 135-degree ledge at the tooth's neck area is also necessary to eliminate possible ceramics braking at the neck-area of the tooth, due to the anatomically small amount of enamel and dentine at this area.

Herein the stump is defined as a natural part of the tooth prepared for a restoration work. Such preparation involves permanently removing a large portion of the tooth's original structure (including portions that might still be structurally sound). The process of preparation usually involves cutting the tooth with special dental burrs, to make space for the planned restorative materials, and to remove any dental decay or portions of the tooth that are structurally unsound. The sides of the stump (like a tooth) will be referred as a proximal, vestibular and oral, see FIG. 3.

ii) an individually customized plastic mesh-tray with a canopy is prepared in the laboratory;

iii) during the second visit, the direct dosage-compensation method of hollow (metal and plastic) volumetric shrinkage of the denture(s) is applied by using a silicone putty to obtain an accurate cast (impression).

The steps of the invention are disclosed below in detail:

1) laboratory preparation of a cast molded plaster model;

2) the cutting a shrink-compensated stump from the cast molded plaster model;

3) performing a circular engraving 0.1-0.15 mm below the limits of the teeth neck area at the cast molded plaster model.

4) a thin pencil drawing is made on 3 sides (proximal, vestibular and oral) of the cut stump's plaster model, as follows:

a) shading of the all plaster model stump's contact sides, forming boundaries of a denture to be made. These shaded areas are define so-called pylons (pylon (Greek) columns supporting arches, arches, floors, bridge spans);

b) on the plaster model stump's vestibular side, connecting (by pencil) the stump(s) contact sides at the level of the teeth neck area, including a clinical neck of the stump. This procedure will form a lower, substantially horizontal (or slightly tilted) latch (cantilever) element, which is similar to ones been used in construction, e.g. in connection of vertical beams in the frame of the building. Such latch of 135 mm width has form 3-4 openings at its end, see 31, FIG. 4.

c) in a similar manner, form a drawing of the upper latch at the plaster model. In this case, the boundaries of the latch are defined by a cutting edge on the incisors and canines, or, alternatively, by the chewing surfaces of molars and premolars. The connecting (by pencil) the stump(s) contact sides will form a several latches, depending on the shape and size of the stump.

d) the drawing of the truss-wall element (half-timber frame pattern, (fachwerk in German)) is made along the median (vertical, horizontal) lines at in the center of the vestibular surface of the stump see FIG. 4.

The fachwerk pattern (or half-timber frame pattern) is defined herein as a lattice of beams filled with a non-load bearing material. it is similar to a known truss structure in engineering, which comprises multiple triangular units constructed with straight members whose ends are connected at joints referred to as nodes. External forces and reactions to those forces are considered acting only at the nodes and result in forces in the members which are either tensile or compressive forces. Moments (torques) are explicitly excluded because, and only because, all the joints in a truss are treated as revolutes. Half-timbered (fachwerk) structures facilitate construction of walls, improving the vertical and horizontal load transmission through the frame. It also provides a spade-shaped border, which is three-times smaller than a vestibular surface total area. Four-element diagonal beams of the frame are defined by pencil connecting the angles of latches and supporting columns (pylons).

e) Then, the middles of diagonal beams should also be vertically connected by a pencil, thus defining the slanted beams of the frame, see FIG. 4.

f) At the lower part (teeth neck) oral surface of the stump, the drawing of the so-called 'garland' should be made. Such garland connects the contact sides of the stump by a strip (ribbon) of 2-2.5 mm width. The rest of the drawing should further be copied similarly to the vestibular surface of the stump. Once wax reproduction of openwork (Bayramov's) frame drawing is finished, a thin layer of insulating colorless varnish is put on the stump followed by a 2-3 min drying procedure.

The final Bayramov's openwork frame will be identical to the described frame's pencil drawing applied to the cast molded plaster model.

The Finishing Steps of the Method are as Follows:

The result of the disclosed method is the fabrication of wax reproductions of the permanent metallic (Bayramov's) openwork frame. The following steps of the disclosed invention are:

5). Accordingly to the aforementioned drawing, the melted wax is put on the stump, precisely along the line that was delineated in drawing, which include lines of the future framework with contours of columns (pylons), latches, beams and diagonal beams, see, 31, 33, 34, 35, 36 FIG. 4. The process is realized using a wax spatula and wax caps, providing a 0.2-0.25 mm of wax layer.

6). The further correction is performed by excess wax removing using a scalpel.

7). Then the final modeling and a "dovetail"—shaping is performed at the wax model's upper latch, which includes:

i) at the corners, closer to the cutting or chewing surfaces, small pearls are applied; ii) At the oral side of the garland area, the final modeling of so-called grips is performed, see 31, 32, FIG. 4. Here the upper part of the garland has a "dovetail"-shaped step to prevent ceramics overlaps, and, ideally, to establish a ceramics butt-joint and a good heat dissipation, see 38, FIG. 4.

8). After the model' correction and preparation, the wax reproduction is removed from the stump and transferred to the laboratory to be replaced by a cast metal denture.

In a specific case of manufacturing bridge prosthetic dentures (not a single tooth, see FIG. 7), the intermediate part of the frames has to be prepared as follows:

i) The premade wax replication of the tooth (so-called inzoma, i.e. Inzoma-Izozit wax structures made by Ivoclar, for example) is inserted into the place of missing teeth at the plaster model. Such inzoma is glued together with the supporting elements, to be included into the whole structure of the openwork frame.

ii) After the full preparation, the wax reproduction of the openwork frame is removed from the model and transferred to the laboratory to be replaced by a cast metallic openwork frame (and subsequent production of the metal openwork Bayramov's frame).

The advantage of the disclosed steps is elimination of openwork metal frame correction, no cast-metal shrinkage and implementation of an anchor-keyed mechanical ligament with coating (ceramic or plastic). Such method uses a novel wax model for the openwork metallic (Bayramov's) frame that can be used in metallic and metalloplastic dental prostheses.

The Laboratory Steps of the Method

The essence of the disclosed laboratory steps of the method is achieving a five-layer ceramic coating (so called 'pie') with interchanging horizontal and vertical directions of the coatings of desired color and shade. The method provides a minimal baking (kiln) time and increased adhesion strength with the aforementioned (Bayramov's) openwork frame. The resulting product (open framework and coating) can serve as a single-tooth, crown-like or micro-prosthetic element or being a part of a larger permanent prosthetic denture.

Further laboratory steps of the disclosed method include laboratory fabrication of two models: the main model and the additional control model to enable a sintering process on the frame.

9). The dental impression herein is a replica of teeth and oral gingival tissue. The first step is a fabrication of a dental gum impression (so-called 'flash-gingiva', i.e. artificial, instantly-made gingival replica that is used as a technological step during the ceramics sintering on the frame), which included the following:

i) on the main model, the separation of the proximal sides of the stump is performed using a dental jigsaw.

ii) at the gingival edge, just below of t stump's neck, a plaster segment is removed by a scalpel in order to form a small area for the impression.

iii) the anatomical cast mold of stump's segment is then removed from the control model using an alginate content material.

The resulting anatomical mold is filled by a plastic mass and glued to the main model for 2 min. This completes the fabrication of the dental impression that replicates completely the gum area around the stump. The impression is tightly fit to the frame and used further for efficient ceramics layering control during its sintering on the frame.

10). At this stage, the openwork frame is located on the main model and the following steps are taken, see FIG. 5:

i) The 1st base coat primer (opaque) layer (see 42, FIG. 5) is applied with a brush on the crown facets of the frame to completely fill the small windows with a vertical application of a very thin layer on the outer surface of the skeleton frame. Such facet can be connected with the frame as a separate element of, for example, a bridge prosthetic denture.

ii) Then, the frame coated with the primer layer is set into an airing cupboard with intensive ventilation having a 100 degrees C. for 10 minutes temperature regime. After that the temperature is decreased to a room temperature with continued ventilation to cool the frame coated by a primer opaque layer.

iii) Immediately after that, the second prime layer (see 43, FIG. 5) is applied in a horizontal direction. Here, the chromatic (color) distribution accordingly to the Table 1. is taken into account for complete covering of the metal surface. The temperature regime is the same as before (for the first primer layer).

iv) Then the third layer (layer (see 44, FIG. 5) is applied vertically, forming a smooth transition from Prime-mass to a Dental-mass. The Prime-mass (the prime) composition is combined with the Dental-mass composition (the dentine) in a 3:1 ratio, respectively, using the color and shade of the main and auxiliary (at the teeth equator) colors as shown in the Table 1. This mass is applied to fill cracks, bowls and shrinkage cavities. The two mentioned compositions are mixed using a sharp-end brush in the presence of distilled water.

v) The resulting composition of the prime/dentine mixture is then used for (spatula) modeling of anatomical features of teeth: angles, grooves, bumps, thereby achieving a smooth bumps transition effect along the edges of the crown and formation of a pit (fissure) which is free of ceramic mass.

vi) The first baling of so-called ceramic 'pie' is than performed.

vii) A fourth horizontal application of prime/dentine mixture layer (see 45, FIG. 5) in a respective 1:2 ratio is followed, using the desired color and shade of the kneading, accordingly to the Table 1. By these means, the near-gingival (i.e. where the dental impression provides a good fit to the frame) part of the frame is modeled, as follows:

By smoothly distribution of the condensed said mixture with a spatula, filling the openwork frame from a buccal side, covering its segments with the transition to the chewing surface of molars and premolars. By these means, so-called "well" is formed based on a proper formation of dental tubercles (a small elevations on some portions of a crown produced by an extra formation of enamel). After that, the inter-proximal segments should be modeled to complete the "well" area. Then an accurate ceramics correction within articulator is performed with respect to antagonists (maxillary/mandibular teeth). An articulator is a mechanical device used in dentistry to which casts of the maxillary (upper) and mandibular (lower) teeth are fixed, reproducing recorded positions of the mandible in relation to the maxilla.

viii) The next step is application and modeling of fifth vertical layer (see 46, FIG. 5) of the Dental-mass composition (the dentine) only using the main and auxiliary colors/shades accordingly to the Table 1. The dentine is applied along a whole circumference of the crown, with the obligatory fitting the main model and impression in order to provide a natural teeth profile (relief).

The residual bottom of the well is further filled by the transparent composition (so-called Schmelz-mass), while a thin layer of dentine is applied at the surface of the tubercles, taking occlusive surfaces of the crown sides into account, see 47, FIG. 5. At this stage, the complete functional area is formed.

ix) After that, the separation of an inter-dental space (up to the prime-mass) is performed, which is followed by a second baking.

x) The final step is a fitting of the main model with the impression, followed by glazing and commissioning the final work to the clinic.

Alternatively to the described composite coating materials, the pyroceram can be used by applying the pyroceram coating layers on the top of the framework's initial drawing.

The advantage of this method is a minimal correction of the ceramic coating, obtaining a five-layers ceramic 'pie' of desired color/shade surfaces with horizontal and vertical composition application, matching the natural teeth color/shade and getting a strong adhesion to the elements of the openwork frame, see FIG. 4-6.

The preparation and application sequence of multilayered ceramic 'pie' as shown in FIG. 5 has been disclosed, including the ratios of the prime vs. dentine compositions and color/shade choice. The color/shade combination be chosen individually, (e.g. using Kerascop by Ivoclar, Table 1). Knowledge of colors and careful application to achieve the visual effect is one of the highlights of working with ceramics. The dentist or dental technician can create a gradation of color (main color near the teeth neck and auxiliary color near the teeth's equator) with a desired level of lightness. The final success of restorative dentistry is determined on the basis of functional and esthetic results. The correct choice of color and shade is essential for achieving good esthetics.

To summarize, the distinguishing features of the disclosed method are as follows:

The main element of the proposed method is a unique openwork (Bayramov's) frame which has a very specific structure that that plays a major role in supporting the resulting denture after applying customized layers of ceramic composition.

The thickness of the openwork frame is 0.28-0.30 mm only, comparing to the 0.4 mm width of the conventional cap. The total thickness of the crown is 0.8 mm comparing to the conventional crown width of 1-1.5 mm.

Another possible application of the disclosed open framework for mini-prosthesis is a management of adjacent teeth' (long axes) convergence, divergence and splinting.

Reduction of the total construction weight of by 30% compare to conventional methods.

Ceramic sintering forms a strong (static) locking the structure based on a pryme/dentine mixture or pyroceram. Such locking provides a supporting element for the denture bridge (several teeth prosthetics).

The minimal kiln-time (limited by two firings procedures) for manufacturing.

Multi-layered ceramic coating of any desired color and shade (Table 1). Main color for neck, auxiliary color for equator areas.

The important feature of the disclosed method is in forming a multi-layered ceramic coating of any desired color and shade (FIG. 5). The coating includes a five ceramic layers with horizontal and vertical application and has a strong adhesive bond (unique frame-lock by a ceramic sintering) with the disclosed Bayramov's open-work frame of fachwerk pattern. Such bond is created by a unique 'static lock' of the frame by a multi-directional ceramics layers.

As the result, unlike conventional approaches, the proposed method enables the disclosed structure to effectively withstand various abrupt dynamic and temperature fluctuations that affect the structure in kiln.

Another advantage of the method is a minimization of the ceramic coating post-correction, using the impression (replica) of the artificial gum (flash-gingiva) for accurate modeling of described multilayered 'ceramic pie', taking the accurate color and shades of the ceramic surface into account before firing and adhesion of the ceramics to the frame.

It is another object of the present invention—an openwork frame made of a sitall. Sitall is crystalline glass-ceramic composition with ultra low coefficient of thermal expansion (CTE). Sitall has a CTE of only $0\pm1.5\times10-7/°$ C. in the temperature range $-60$ to $60°$ C., placing it in a rather small group of transparent materials with low CTE such as Pyrex Zerodur, Cervit and fused quartz.

In case of the sitall implementation, the dental gum-impression is taken during the first patient's visit in order to cast both the main and control models in the laboratory, as described before. Then, the segment with prepared teeth (stumps) is separated from the impression using a special separating spatula at the main model. After that, the separated segment is filled with the fireproofed composition, having stud(s) being preliminary installed into the composition. After drying, the impression (with a fireproofed segment) is cast with gypsum, essentially completing a so-called 'combined model'.

Furthermore, the openwork frame drawing is imposed on the fireproof control model, as has been described before, but using a sitall-emulsion pencil. The sitall emulsion is a composition of: water—15%, sital—35% and glycerin—50%. Then, the fireproofed segment with stud(s) is removed from the main model and inserted into the vacuum oven for 950-1100 C degree firing, to produce an openwork frame made of sitall. After that, the described multilayered ceramics coating is applied, in order to obtain a sitall-ceramics construction.

In case of using a bridge-type denture (multiple teeth replacement, FIG. 7), the wax replica (inzoma) is inserted into the intermediate part of the model to make an alginate impression. Afterwards, the wax is removed from the impression, while the impression is filled with the sitall emulsion to be dried in the oven. Such sitall inszoma is inserted into the fireproofed model and fixed by a sitall emulsion during a subsequent firing of the final sitall openwork frame in a vacuum oven.

The advantage of the described sitall openwork frame is a complete eliminating of metallic elements (and its shrinking), as well as achieving an excellent sitall-ceramics bonding. Another advantage of sitall is in effective treatment of defects with multiple teeth defects, as well as in cases with metal-related allergy.

Moreover, the obvious advantage of the sitall composite openwork (Bayramov's) frame is its applicability towards the various kinds of dental prosthetic devices, fast and efficient manufacturing process, and a reduced material and time consumption.

The disclosed method is an indispensible dental tool which developed to better satisfy the requirements related to the modern dentistry, both in functional and aesthetic aspects. It is based on a novel approaches to teeth' preparation (less aggressive turning) and better natural teeth tissue preservation of the teeth' (masticatory apparatus) functionality.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A denture, comprising:
   an openwork frame adapted to be placed on at least one tooth, wherein said frame comprises a fachwerk pattern; said fachwerk pattern comprising a lower latch to be positioned to extend along a ledge formed at the tooth's equator and an upper latch to be positioned at a cutting edge of the tooth, said fachwerk pattern further comprising pylons that extend substantially vertically from the lower latch to the upper latch and intersecting diagonal beams that extend from the lower latch to the upper latch with a shield covering the intersection of the diagonal beams for strengthening the frame;

wherein said frame is cast as a single piece;

wherein said fachwerk pattern provides for a lightweight structure in comparison with a cast solid structure;

wherein said frame is customized for a patient's tooth size and shape;

a multi-layered ceramic coating covering the openwork frame and penetrating into open part of the cast thus providing an improved ceramic-frame adhesion.

2. The denture of claim 1, wherein the openwork frame is made of metal or metal alloy.

3. The denture of claim 1, wherein the openwork frame comprises at least four diagonal beams coming from four corners of a tooth neck and being connected together at a cutting edge of the tooth.

4. The denture of claim 3, further comprising: a supporting shield covering an intersection of the diagonal beams for strengthening the lightweight structure.

5. The denture of claim 3, further comprising: upper cantilevers at a cutting edge of the tooth which connect ends of the diagonal beams providing a rigid lightweight structure.

6. The denture of claim 5, wherein pearls are placed in corners where the diagonal beams and the upper cantilevers are connected; wherein said pearls are bead-shaped elements of the open frame designed to create unbreakable ceramics.

7. The denture of claim 6, further comprising: diagonal struts connecting the diagonal beams for strengthening the lightweight structure.

8. The denture of claim 7, wherein openwork frame is intended to be placed on the ledge of the stump located at the tooth's equatorial region.

9. The denture of claim 8 is adapted to be placed on the 135 degree ledges located at the tooth neck and at the tooth equatorial region.

10. The denture of claim 3, further comprising:

a lower cantilevers located at the lower part of the denture which are intended to be spatially corresponding to the tooth neck at an oral part of the structure;

wherein said lower cantilever comprises of the plurality of holes which provide improved frame-coating adhesion creating therein additional adhesion;

wherein said lower cantilevers are additionally intended for heat dissipation and thus prevents ceramic material from cracking.

11. The denture of claim 1, wherein the openwork frame is adapted to be placed on a tooth stump; wherein said frame comprises of a garland intended to specially correspond to the lower ledge of the tooth stump's neck on its vestibular side; wherein garland is to be placed on said ledge.

12. The denture of claim 1, wherein the openwork frame is made of sitall.

13. The denture of claim 1, wherein the multi-layered ceramic coating includes:

a basic first prime opaque layer that fills windows of the frame and is applied vertically on the frame;

a second prime opaque layer, the second prime layer is matched to a color palette of the tooth and is applied horizontally on the basic first prime opaque layer;

a first mixed opaque-dentine composition layer, and is applied vertically on the prime opaque layer;

a second mixed prime opaque-dentine composition layer, and is applied horizontally on the first mixed prime opaque-dentine composition layer;

a mixed dentine layer, the mixed dentine layer made of a main dentine and an auxiliary dentine and vertically is applied on the second mixed prime opaque-dentine composition layer;

a transparent layer is applied on the mixed dentine layer forming a tooth shape wherein said multilayer coating acts as a self-interlocking mechanism with the said open frame.

14. The denture of claim 13, wherein the first mixed opaque-dentine composition layer being in the 3:1 respective ratio.

15. The device of claim 13, wherein the mixed dentine layer made of the main dentine and the auxiliary dentine in the 3:1 respective ratio.

* * * * *